United States Patent [19]
Eccles et al.

[11] Patent Number: 5,500,351
[45] Date of Patent: Mar. 19, 1996

[54] BIOSENSORS FOR DETECTING METAL IONS CAPABLE OF BEING REDUCED BY REDUCTASE ENZYMES

[75] Inventors: Harry Eccles; Geoffrey W. Garnham, both of Salwick; Christopher R. Lowe; Neil C. Bruce, both of Cambridge, all of United Kingdom

[73] Assignee: British Nuclear Fuels PLC, Warrington, United Kingdom

[21] Appl. No.: 276,322

[22] Filed: Jul. 18, 1994

[30] Foreign Application Priority Data

Jul. 22, 1993 [GB] United Kingdom ............... 9315183

[51] Int. Cl.$^6$ ............... C12Q 1/26; C12N 9/88; G01N 27/00
[52] U.S. Cl. ............... 435/25; 435/189; 435/232; 435/288.7; 435/817; 435/287.1; 204/403; 205/777.5
[58] Field of Search ............... 435/25, 189, 190, 435/232, 288, 817; 204/153.12, 403

[56] References Cited

U.S. PATENT DOCUMENTS

| | | | |
|---|---|---|---|
| 4,614,714 | 9/1986 | Rusakabe | 435/25 |
| 5,217,594 | 6/1993 | Henkens | 204/403 |

OTHER PUBLICATIONS

Blum, L., Design of Luminescence Photobiosensors J of Biolium & Chemilum 4: 543–550 (1989).
Bacdi F., Environmental Applications of Mercury–Water Air & Soil Pollution 56: 465–475 (1991).
Ryabov, A., Biochemistry of Organometallic CPDS Biochemistry USSR vol. 55 No. 7 Pt 1 (1994) pp. 863–930.
Vo, M., Preparation and Properties of Immobilized . . . Nippon Seramikkusu Kyokai 100: 430–433 (1992).

*Primary Examiner*—Ralph J. Gitomer
*Attorney, Agent, or Firm*—Nixon & Vanderhye

[57] ABSTRACT

A biosensor for detecting metal ions of elements such as Hg, Cr, As, Tc, Cu, Ag, Se, V, Mo and U which are capable of being reduced to metal by a reductase enzyme. The reductase enzyme is contained in an immobilized enzyme composition also including a cofactor and a coenzyme. The cofactor, for example NADPH, is oxidized by a reaction coupled with the reductase reduction of the metal ions and the cofactor in its oxidized state, e.g., NADP$^+$, is re-reduced thereby maintaining a supply of the reduced state cofactor by action of the coenzyme in a further oxidation reaction coupled with the cofactor reduction. The further oxidation reaction may be oxidation of an alcohol to an aldehyde brought about by a dehydrogenase coenzyme. The oxidation brought about by the coenzyme, i.e., the amount of oxidized product, is a measure of the amount of oxidized state cofactor produced which, in turn, is a measure of the concentration of metal ions being detected. The amount of oxidation may be detected in one of a number of ways, especially by coupling the oxidation product with a reaction catalyzed by a light emitting coenzyme such as luciferase.

18 Claims, 4 Drawing Sheets

BIOSENSORS FOR DETECTING METAL IONS CAPABLE OF BEING REDUCED BY REDUCTASE ENZYMES

BIOSENSORS

The present invention relates to biosensors and more particularly to biosensors for detecting metal, especially heavy metal, ions.

In one known form of biosensor described in European Patent No. 263948 and incorporated by reference herein, a reactive biochemical component in the form of a peptide from the group of phytochelatines is immobilised on a transducer. On contact with aqueous solutions of heavy metal ions, complexes with the phytochelatin lead to a change in the transducer output and hence provide a rapid analysis of heavy metal ions. However, detection in this way is not specific to individual metal species and furthermore when the peptide combines with the heavy metal ion it is very different to separate the heavy metal from the complex formed, eg if it is necessary to make further measurements using the peptide.

The purpose of the present invention is to provide an improved biosensor in which these problems are avoided.

According to a first aspect of the present invention, a biosensor comprises a biochemical capable of producing a biochemical reaction in the presence of metal ions and a transducer arranged to detect transducible output agent produced directly or indirectly by the reaction produced by the biochemical in the presence of metal ions characterised in that the biochemical comprises an enzyme which is a reductase for the metal to be detected.

According to the present invention in a second aspect there is provided a method of detecting metal ions, the method comprising exposing to the metal ions a biosensor as in the first aspect thereby causing the reductase enzyme to induce a reduction of the metal ions and thereby produce directly or indirectly a transducile output agent, the output agent being detected by the transducer of the biosensor.

The metal ions detected in accordance with the present invention may be ions of mercury, chromium, arsenic, technetium, copper, silver gold, selenium, vanadium, molybdenum or uranium. Reductase enzymes for the biochemical reduction of each of these metal species are known per se from the literature. The metal species to be detected may be present in a given sample, eg aqueous solution, to be investigated as simple metal ions or as compounds or complexes, eg organometallics.

Where the metal species to be detected is present as a compound or complex it may be desirable to employ another chemical or biochemical agent, eg an enzyme, to convert the compound or complex into its simple metal ion state so that it may be detected by the reductase enzyme. For example, mercuric lyase may be employed to convert mercury organometallics to simple mercuric ions which may be detected by mercuric reductase.

In contrast with the prior art technique described in the aforementioned EP specification the present invention allows metal ion detection which can be highly specific to the metal species of interest. Thus, for example, mercuric reductase is highly specific to the presence of mercuric ions, Furthermore, the metal obtained from the reduction process involving use of the reductase enzyme can be separated, concentrated and if necessary recycled from the medium in which it is originally present.

The biosensor in accordance with the first aspect of the present invention may need to employ together with the metal reductase a co-enzyme which is an electron source for the metal ion reduction process. The co-enzyme may itself produce or may produce via one or more other co-enzymes in a co-enzyme chemical chain a signal which may be detected by the transducer.

The reductase may be employed together with the nicotinamide enzyme NADPH as a co-enzyme which is oxidised to $NADP^+$ by the reduction of the metal species to be detected, eg Hg(II) to Hg (O) by mercuric reductase. The production of $NADP^+$ may be detected by oxidation of a further reductant, the oxidation thereby producing directly or by inducing the one or more further oxidation-reduction reactions, one of the output agents produced above.

Examples of enzyme-induced oxidation-reduction chains involving the use of reductase and NADPH are given below.

The transducer may comprise a detector which detects a transducible output agent produced in a reaction involving a chemical change in a co-enzyme associated with the reductase or a co-enzyme thereof and brought about directly or indirectly by the reduction produced by the reductase. The said output agent may comprise for example photons which may be detected by a known photodetector, eg a luminometer. Alternatively, the output agent may comprise electrons which may be detected by a known amperometric arrangement comprising an electron sensitive electrode. The output agent could alternatively comprise protons, ions, heat or mass each of which may be continuously sensed as produced in real time.

Where the reductase is mercuric reductase it may be employed together with the nicotinamide enzyme NADPH as a co-enzyme which is oxidised to $NADP^+$ by the reduction of Hg(II) to Hg(O) by mercuric reductase. The production of $NADP^+$ may be detected by oxidation of a further reductant the oxidation thereby producing directly or by inducing of further oxidation-reduction reactions one of the output agents produced above.

Examples of enzyme induced oxidation-reduction chains involving the use of mercuric reductase and NADPH are given below.

Sources of mercuric lyase and mercuric reductase for the detection of mercury in the manner described above are known. However, mercuric lyase and reductase may be made by a molecular cloning technique in which DNA fragments encoding the lyase and reductase genes are inserted in vitro into cloning vector molecules. The recombinant mercuric lyase and reductase clones are isolated and subjected to physical and functional characterisation with a series of subcloning procedures. Finally, the cloning entails the incorporation of transcriptional and translational signals, since the cloned coding sequences of mercuric lyase and mercuric reductase should have strong endogenous transcriptional and translational signals appropriate to the host.

The biosensor of the first aspect of the present invention with its specificity for given metal ions has many potential applications for the detection of any of the metals having a suitable reductase enzyme, eg those specified above. Mercury for instance is one of the more toxic metals present in significant quantities in the environment and is desirable to be able to detect accurately in many situations. Mercury is toxic to organisms even at very low concentrations, and unlike many of the other heavy metals, has no known beneficial biological function. Metallic mercury is somewhat less reactive with biological systems than the ionic or organic forms. In higher concentrations, mercury is biocidal, whilst lower concentrations of mercuric ions are mutagenic and teratogenic (Summers, 1986). Increases of several thousand-fold in the concentration of $Hg^{2+}$ ions above background levels are attributable to the use of mercurial fungicides in papermaking and agriculture, mercury catalysts in industry, and due to the use of disinfectants in hospitals. In the chloroalkali industry alone, over 15 g of mercury in the form of mercuric ion may be lost to the environment for every ton of chlorine produced (Murozumi, 1967). The most common inorganic mercuric salt is HgS, comprising up to 7% mercury by weight of the ore, red cinnabar. Some $10^{10}$ tons of rock (average 80 μg Hg/kg) are weathered globally each year releasing 800 tons of Hg(II) into the environment; the oceanic reservoir of mercury is estimated at 200 million tons. The dissolved Hg(II) concentration in water typically ranges from 0.03 to 2.0 μg/liter (ie, up to $10^{-8}M$). Mercury naturally exists in the environment predominantly as methyl mercury, arising from biomethylation of mercuric ions via methyl $B_{12}$ in sewage and sediments (Ridley et al., 1977). Aryl mercurials are industrial contaminants, for example from the paper industry. These organomercurial compounds are toxic partly due to their ligation to thiol groups in proteins and partly due to their lipophilicity which allows them to readily pass through biological membranes, and leads to their accumulation in the food chain (McAuliffe, 1977). Methyl mercury is 50 to 100 times more toxic than inorganic $Hg^{2+}$ and resulted in human poisonings at Minimata and Niigata in Japan in the 1950's from ingestion of seafood containing methylmercuric compounds. Later, in Iraq, similar poisonings were attributed to the use of flour treated with alkylmercury fungicides.

According to one particular form of the present invention there is provided a method of detecting a metal species of interest, the method comprising exposing to the ions of the species to be detected a biosensor as in the first aspect thereby causing the reductase enzyme to induce a reduction of the metal species and thereby produce by oxidation of the co-enzyme an output of photons, and detecting the output photons by a photodetector.

The said co-enzyme may itself produce the said photons or these may be produced via one or more other co-enzymes acting in a co-enzyme bio-chemical chain.

The said photons may be produced by the enzyme luciferase. This may be employed in a biochemical chain reaction together with NADPH for example in the manner described below.

The reductases in the said particular form of the present invention may conveniently be employed together with the nicotinamide enzyme NADPH as a co-enzyme which is oxidised to $NADP^+$ by the reduction of metal ions by the reductase. The production of $NADP^+$ may be detected by oxidation of a further reductant, the oxidation thereby producing directly, or by inducing of further oxidation-reduction reactions, the said output photons.

For example, the production of $NADP^+$ may be detected by the oxidation of an alcohol, eg a primary or secondary alcohol, eg an aliphatic alcohol such as hexanol or octanol, to its corresponding aldehyde, eg in the presence of an alcohol dehydrogenase, eg TADH which is obtained from *Thermoanaerobium brockii*. The aldehyde so produced may be detected by reaction with reduced flavin $FMNH_2$ in the presence of oxygen together with the enzyme luciferase to catalyse the reaction. Luciferase may be obtained from *Vibrio harveyi*, and is commercially available. It is very sensitive to the presence of aldehyde and can detect concentrations as low as pmol quantities providing light emission from the reaction it catalyses. The intensity of emitted light provides a measure of the $NADP^+$ converted to NADPH which in turn provides a measure of metal ion concentration present. Examples of such reaction chains are illustrated below.

In the biosensor according to the first aspect of the present invention it is desirable to immobilise and stabilise the biochemical agent(s) in close proximity to the transducer so that the enzymes remain active for long periods (eg months or years) and are not lost from the sensor. As in the prior art, immobilisation may be achieved by adsorption on an organic or inorganic carrier, physical inclusion in a gel, behind a semi-permeable membrane, cross-linking by bifunctional or multifunctional reagents or covalent bonding to the transducer either directly or using a linker.

Where the transducer comprises an electrode, the electrode may for example comprise tungsten or glassy carbon or discs or wires or metal printed onto plastics or alumina substrates. The biochemical may in suitable cases be deposited, eg by screen printing onto the electrode.

BRIEF DESCRIPTION OF THE DRAWINGS

Embodiments of the present invention will be described by way of example with reference to the accompanying drawings, in which.

DETAILED DESCRIPTION OF THE INVENTION

Figure 1:
FIG. 1 is a cross-sectional end view of a biosensor arrangement embodying the present invention.

As shown in FIG. 1 a biosensor comprises an immobilised and stabilised enzyme layer 1 incorporating a metal reductase deposited on (the underside of) an electrode 2 providing a substrate therefor and a semi-permeable membrane 3 covers the layer 1.

The layer 1 in use contacts via the membrane 3 a sample of aqueous solution possibly containing the metal ions required to be detected. By a series of biochemical reactions in one of the ways described hereinafter metal ions are reduced to metal by the layer 1 and electrons are produced as a result, the number of electrons produced being a measure of the concentration of the metal ions. The electrode 2 is connected (not shown) to a potentiostat which in turn provides an output voltage signal to a display (not shown) the magnitude of the signal being a measure of the detected metal ion concentration.

Figure 2:
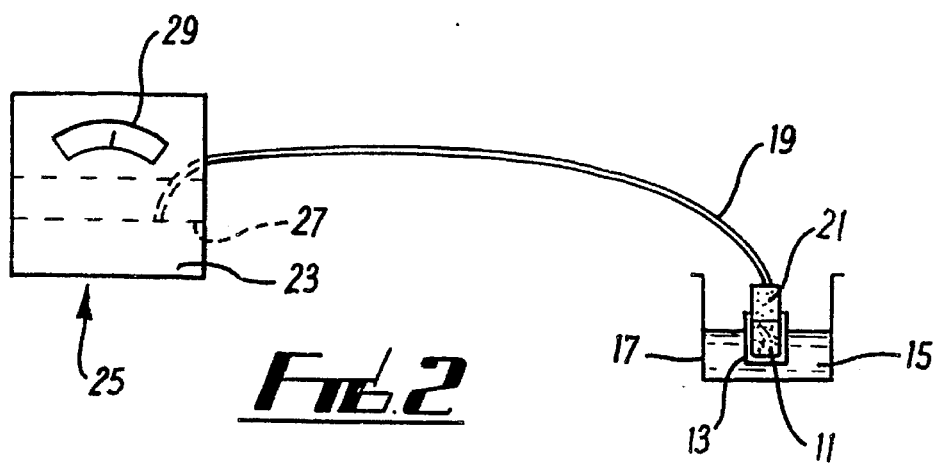
FIG. 2 is a side view of another biosensor arrangement embodying the present invention.

As shown in FIG. 2, another biosensor arrangement comprises an immobilised and stabilised enzyme layer 11 incorporating a reductase which is coated with a semi-permeable membrane 13 in a sample 15 of an aqueous solution to be investigated held in a vessel 17. A fibre-optic cable 19 is fitted via a ferrule 21 to make contact at one of its ends with the layer 11 the other end of the cable 19 being connected to a photodetector 23 incorporated within a luminometer 25. Outputs from the photodetector 23 are processed by an electronics unit 27 within the luminometer 25 and output signals are visually indicated on a display 29.

In use of the arrangement shown in FIG. 2, metal ions to be detected in the sample 15 are reduced in one of the ways described herein by the enzymes in the layer 11 and photons are produced by an appropriate series of chemical reactions, the number of photons being a measure of the concentration of the metal ions present. The photons are detected by the photodetector 23 via the cable 19 and the output of the photodetector is employed to operate the display 29 to give an indication of the level of the concentration of metal ions detected.

Figure 3:
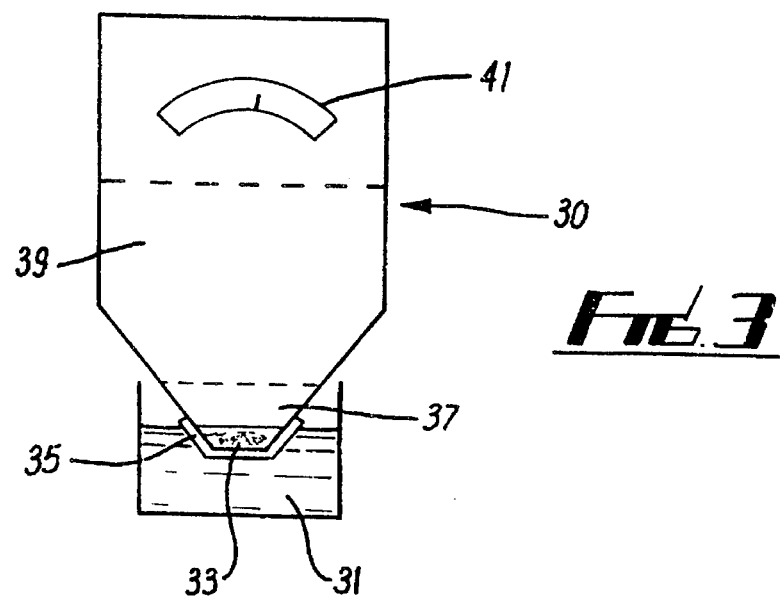
FIG. 3 is a side view of an alternative biosensor arrangement embodying the present invention.

The arrangement shown in FIG. 3 is similar to that shown in FIG. 2 except that the immobilised enzyme layer forms part of the luminometer indicated in FIG. 2 by numeral 30 and so no fibre-optic cable is required between the two. Thus, in FIG. 3, metal ions in a sample 31 are converted by a stabilised and immobilised enzyme layer 33 with which they make contact via a semi-permeable membrane 35 and resulting photons generated in the layer 33 are detected directly by a photodetector 37 adjacent to the layer 33 which via an electronics unit 39 provides an output signal for indication on a display 41.

Examples of immobilised enzyme layers for use in the above embodiments will now be described. In each of the following examples it is assumed that metal ions already exist. Other enzymes may be required to break down complex or compound metal species to metal ions to begin the process. For example, mercuric lyase may be used in conjunction with mercuric reductase to convert organomercurials into simple mercuric ions where it is required to detect mercury.

EXAMPLE 1

Diaphorase/methylviologen (MB) Coupled System

Figure 4:
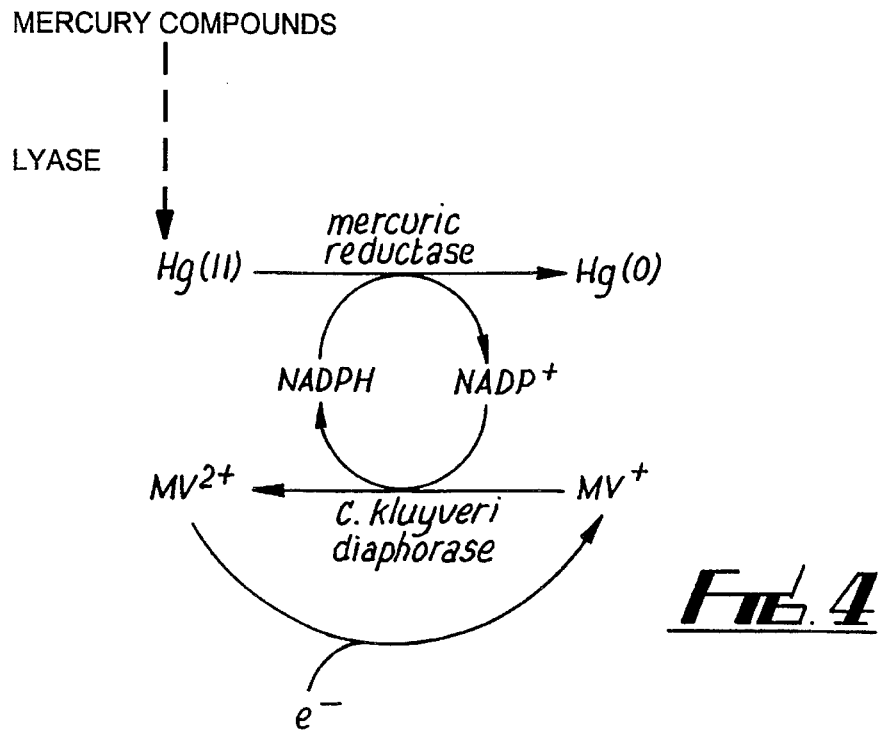
FIGS. 4 to 7 are diagrammatic representations of biochemical reactions which may be employed in biosensors embodying the present invention.

This example is illustrated in FIG. 4. The reductase is employed together with NADPH to detect metal ions in a given sample.

The reductase brings about the reduction of metal ions and the enzyme NADPH is concomitantly oxidised to $NADP^+$. This oxidised product is re-reduced to NADPH by diaphorase from *Clostridium kluyveri* and the one-electron reductant ($MV^+$) of methylviologen ($MV^{2+}$). Electrons released from the methylviologen oxidation are employed to indicate the concentration of metal ions present, eg in the manner described with reference to FIG. 1.

EXAMPLE 2

Peroxide Coupled System

Figure 5:
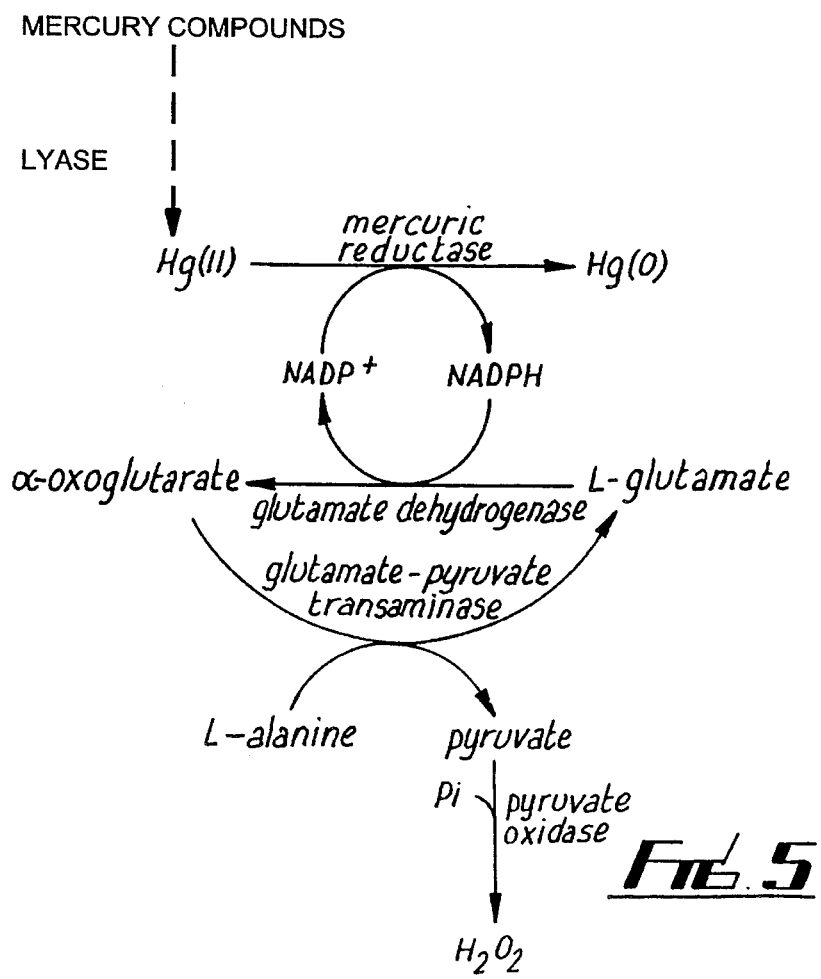

This example is illustrated in FIG. 5. In this case the metal reductase again reduces the metal ions to be detected and NADPH is oxidised to $NADP^+$. The oxidised coenzyme $NADP^+$ is re-reduced enzymically with L-glutamate dehydrogenase (eg from bovine liver), glutamate-pyruvate transaminase (eg from pig heart) and pyruvate oxidase (eg from Pediococcus spp).

The product is $H_2O_2$ as illustrated in FIG. 5 and the concentration of this product may be measured directly, eg on a platinum electrode at 0.7V or via a mediatorless peroxidase electrode using a fungal peroxidase obtained from Arthromyces ramosus for the oxidation of $H_2O_2$ in a phosphate buffer solution at pH 7.0. The electrode and enzyme layer may be arranged as shown in FIG. 1.

EXAMPLE 3

Luciferase Bioluminescent Coupled System Involving Octanol

Figure 6:
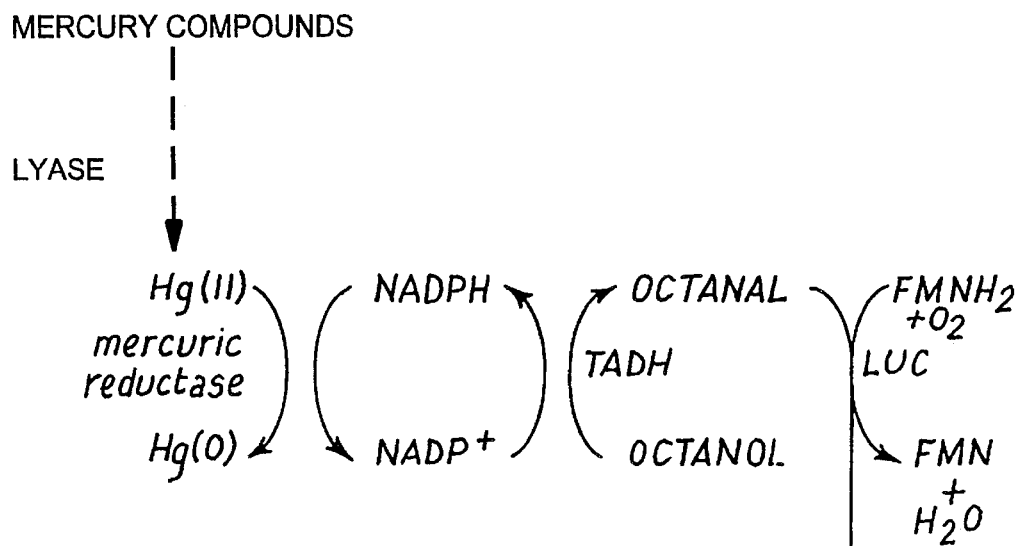

This example is illustrated in FIG. 6. In this case the reductase reduces the metal ions to be detected and NADPH is again oxidised to NADP+. This oxidised product is re-reduced by the oxidation of octanol to octanal brought about by the co-enzyme alcohol dehydrogenase, e.g. obtained from the commercially available *Thermoanaerobium brockii*.

The alcohol dehydrogenase is represented in FIG. 6 by TADH. The octanal is reacted with reduced flavin, $FMHN_2$, in the presence of oxygen and catalysed by luciferase, LUC and the products octanoic acid, FMN oxidoreductase and water are produced as illustrated in FIG. 6 and light is caused to be generated and this may be detected in the manner described with reference to FIG. 2 or FIG. 3.

As noted above, bioluminescent biosensors promise high specificity due to the enzymic reaction and a sensitivity sufficient to register quanta of light. Luciferase is preferably the enzyme responsible for the light-emitting reaction of luminous bacteria and may be employed as illustrated in FIG. 6 to catalyse the reaction of molecular oxygen with reduced flavin and aliphatic aldehyde to form long-lived intermediates whose breakdown provides energy to give light emission with reasonably high quantum yield ($\approx 10\%$), as follows:

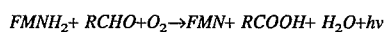

$$FMNH_2 + RCHO + O_2 \rightarrow FMN + RCOOH + H_2O + hv$$

RCHO represents the aliphatic aldehyde and hv represents light.

The reduced flavin is generated in situ by specific NAD(P)H: FMN oxidoreductases

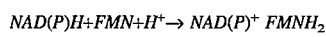

$$NAD(P)H + FMN + H^+ \rightarrow NAD(P)^+ \; FMNH_2$$

and thereby coupled in with the target system via the $NADP^+$ dependent alcohol dehydrogenase.

EXAMPLE 4

Luciferase Bioluminescent Coupled System for Nitrite Reduction

Figure 7:
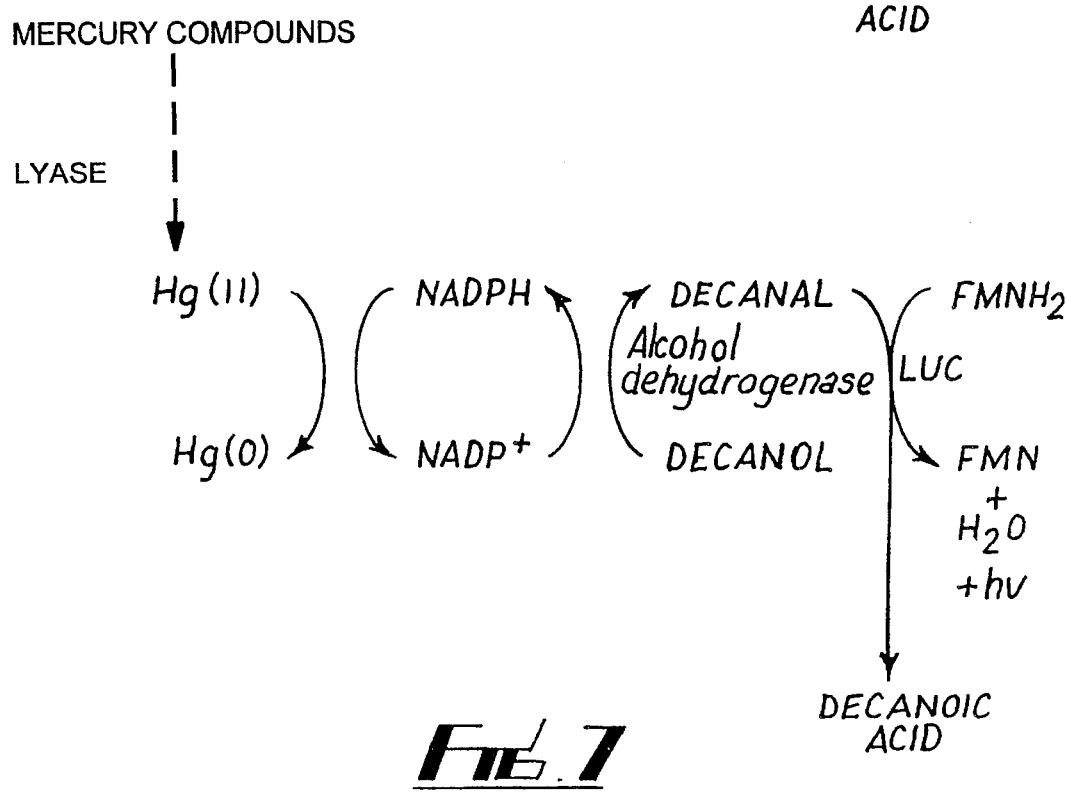
Figure 8:
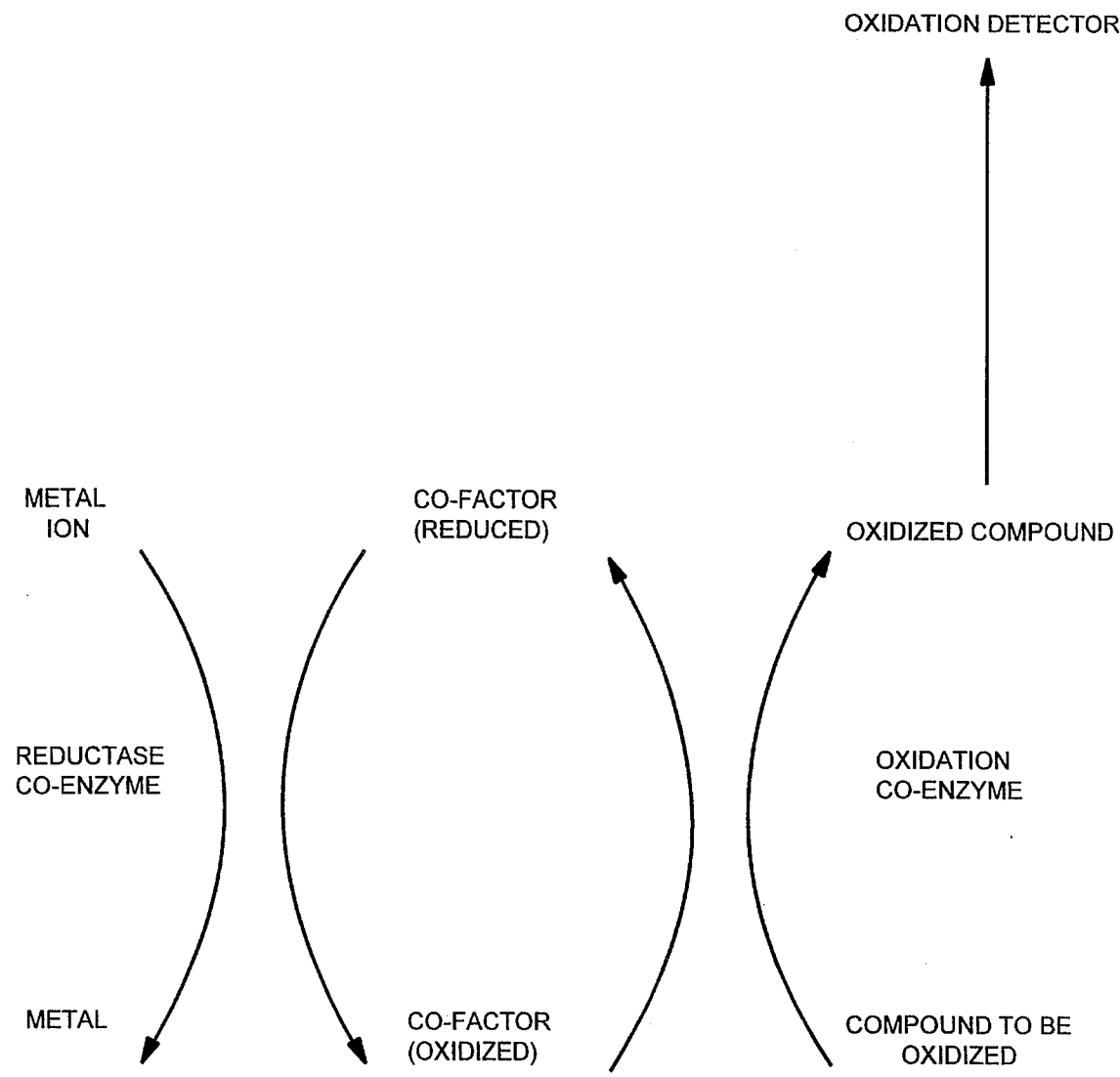
FIG. 8 illustrates a general reaction scheme illustrating operation of a biosensor according to the present invention. A metal ion, e.g., an ion of ttg, Cr, As, Tc, Cu, Ag, Au, Se, V, Mo or U, to be detected is reduced by a metal reductase coenzyme to metal with concomitant oxidation of a cofactor to its oxidized state, e.g., from NADPH to $NADP^+$. The amount of cofactor in the oxidized state is detected by re-reduction of the cofactor to its reduced state, thereby maintaining a supply of the cofactor in that state, by the action of an oxidation of coenzyme which concomitantly brings about oxidation of a compound to be oxidized to an oxidized compound. The amount of the oxidized compound produced is detected directly or indirectly by an oxidation detector in one of the ways described above. For example, the compound to be oxidized may be an alcohol, the oxidation coenzyme may be an alcohol dehydrogenase and the oxidized compound may be an aldehyde.

This example is illustrated in FIG. 7. The process is carried out in a manner similar to that illustrated in FIG. 6 except that in this case the re-reduction of $NADP^+$ is brought about by the oxidation of decanol to decanal by the co-enzyme dehydrogenase, eg obtained from the commercially available *Thermoanaerobium brockii*.

We claim:

1. A biosensor for detecting ions of a metal capable of being reduced by a metal reductase enzyme, the biosensor comprising:

an immobilized enzyme composition comprising a metal reductase enzyme, a cofactor having a reduced state and an oxidized state and which is converted from its reduced state to its oxidized state by the reduction of metal ions by said metal reductase enzyme, a first coenzyme capable of inducing an oxidation reaction in the presence of the cofactor in its said oxidized state, thereby being converted to its reduced state to maintain a supply of the cofactor in its reduced state to permit further reduction of the metal ions by the reductase enzyme, and means for detecting oxidation induced by the second coenzyme, oxidation by the second coenzyme being a measure of formation of the first coenzyme in its oxidized state which, in turn, is a measure of metal ions reduced by said metal reductase enzyme.

2. The biosensor as in claim 1 wherein said metal ions are selected from the group consisting of mercury, chromium, arsenic, technetium, copper, silver, gold, selenium, vanadium, molybdenum and uranium.

3. The biosensor as in claim 1 wherein the metal ions to be detected are present as a complex or a compound and the biosensor further includes a third coenzyme to covert the complex or compound into its sample metal ion state so that it may be detected by the reductase enzyme.

4. The biosensor as in claim 3 wherein mercury ions are detected, the enzyme is mercuric reductase and the third coenzyme is mercuric lyase to convert organomercurials to simple mercuric ions which may be detected by the mercuric reductase.

5. The biosensor as in claim 1 wherein said cofactor comprises NADPH in its reduced state, its oxidized state being $NADP^+$.

6. The biosensor as in claim 5 wherein the second coenzyme comprises an enzyme which oxidizes a reduced form of methylviologen, the reduced form of the methylviologen being added to the enzyme composition, and the means for detecting the extent of oxidation comprising an electrical detector for detecting the quantity of electrons released in said oxidation.

7. The biosensor as in claim 6 wherein said second coenzyme comprises diaphorase.

8. The biosensor as in claim 4 wherein said second coenzyme comprises a dehydrogenase, and L-glutamate is added to said immobilized enzyme composition to produce $H_2O_2$ in response to production of α-oxoglutarate, and said enzyme composition also contains a composition to produce $H_2O_2$ in response to the production of α-oxoglutarate, and the means for detecting the extent of oxidation comprising an electrical detector for detecting $H_2O_2$ produced.

9. The biosensor as in claim 8 wherein the composition producing $H_2O_2$ comprises glutamate-pyruvate transaminase, L-alamine and pyruvate oxidase.

10. The biosensor as in claim 5 wherein said enzyme composition also comprises a luminescent coenzyme which produces a light emission in response to oxidation by said second coenzyme, and said means for detecting the extent of oxidation comprising a photon detector for detecting photons emitted by the luminescent coenzyme.

11. The biosensor as in claim 10 wherein the luminescent enzyme comprises luciferase.

12. The biosensor as in claim 11 wherein the said second coenzyme comprises an alcohol dehydrogenase and an alcohol to be oxidized by the second coenzyme is also contained in the enzyme composition.

13. The biosensor as in claim 12 wherein the enzyme composition also contains a chemical oxidized by an aldehyde in the presence of the luciferase and photons produced by the luciferase in oxidation of said chemical is a measure of the amount of said alcohol converted into aldehyde by the dehydrogenase.

14. The biosensor as in claim 13 wherein the chemical oxidized by the aldehyde is reduced flavin.

15. The biosensor as in claim 12 wherein the alcohol is decanol.

16. The biosensor as in claim 12 wherein the alcohol is octanol.

17. A method of detecting metal ions comprising the steps of:

(a) exposing metal ions to be detected to a first coenzyme, which is a reductase for the metal ions, thereby reducing the metal ions, reduction in the presence of a cofactor having a reduced state and an oxidized state, the cofactor being converted from its reduced state to its oxidized state, in conjunction with metal ion reduction;

(b) re-reducing the cofactor from its oxidized state to its reduced state to maintain a supply of the cofactor in its reduced state to permit further reduction of the metal ions by the first coenzyme reducing, said re-reducing being in the presence of a second coenzyme which causes a concomitant further oxidation reaction; and (c) measuring oxidation brought about by the second coenzyme indicating cofactor produced in its reduced state, which in turn gives a measure of the metal ions present.

18. A method of detecting metal ions comprising the steps of (a) exposing metal ions to be detected to a reductase for the metal ions thereby reducing the metal ions, the reduction being in the presence of nicotinamide cofactor NADPH which is thereby oxidized to $NADP^+$;

(b) re-reducing the $NADP^+$ produced to NADPH by oxidation by an alcohol dehydrogenation coenzyme in oxidizing an alcohol to an aldehyde, the aldehyde thereby produced being a measure of the $NADP^+$ produced;

(c) oxidizing the aldehyde in the presence of a light emitting coenzyme; and (d) detecting the photons emitted by the light emitting coenzyme, the number of photons being a measure of the aldehyde produced.

\* \* \* \* \*